United States Patent [19]

Silbering et al.

[11] Patent Number: 4,499,067

[45] Date of Patent: Feb. 12, 1985

[54] ORAL COMPOSITIONS COMPRISING $N^G$-ACYL DERIVATIVES OF ARGININE

[75] Inventors: Steven B. Silbering, Plainsboro; Tibor Sipos, Lebanon, both of N.J.

[73] Assignee: Johnson & Johnson Products, Inc., New Brunswick, N.J.

[21] Appl. No.: 412,048

[22] Filed: Aug. 26, 1982

[51] Int. Cl.$^3$ .............. C07C 129/12; A61K 7/18; A61K 7/22

[52] U.S. Cl. .............. 424/52; 424/54; 260/404.5; 562/560

[58] Field of Search .............. 562/560; 424/52, 54; 260/404.5

[56] References Cited

U.S. PATENT DOCUMENTS 2,772,203 11/1956 Salzmann .............. 424/54

OTHER PUBLICATIONS

Guttmann, Acta Chim Acad. Sci. Hung, 44, pp. 23–30, (1965).
Yoshida, Chem. Abst., 85:110386, (1976).
"Beilstein Handbuch der Organischen Chemie", 2nd Supp., vol. 4, pp. 1354–1361, (1963).
"Beilstein Handbuch der Organischen Chemie", 3rd Supp., vol. 4, p. 2652, (1980). •

Primary Examiner—Michael L. Shippen

[57] ABSTRACT

Oral hygiene formulations incorporating $N^G$-acyl derivatives of arginine, or the pharmaceutically acceptable salts thereof, optionally in combination with fluoride compounds, are effective in combatting microorganisms, inhibiting acid production and reducing dental caries.

32 Claims, No Drawings

ORAL COMPOSITIONS COMPRISING $N^G$-ACYL DERIVATIVES OF ARGININE

FIELD OF THE INVENTION

The present invention relates to compositions of matter having utility in maintaining oral health. It also relates to methods of making such compositions, and the incorporation of same into pharmaceutically suitable vehicles for use in oral health care. More particularly, the invention relates to acyl derivatives of arginine, optionally in combination with fluoride compounds, and their utility in maintaining oral health.

BACKGROUND OF THE INVENTION

It has been shown that tooth decay and dental disease can be attributed to bacteria forming plaque about the teeth. Growth and proliferation of bacteria is enhanced by the presence of entrapped food particles between the teeth. The removal of plaque and entrapped food particles reduces caries, reduces the tendency towards gingivitis, and reduces mouth odor as well as generally improving oral hygiene.

The prior art recognizes mechanical oral hygiene devices serving to clean the mouth of debris and remove plaque from teeth, such as toothbrushes, flosses, and toothpicks. It also recognizes compositions mostly used in conjunction with such devices but which impart a chemical action in cleaning teeth, such as dentifrices and rinses. In addition to these, various dental coatings and sealants have been applied to teeth as barriers against bacterial action and plaque formation. Another important approach in oral care includes the use of various fluoride-containing preparations which are able to deposit fluoride ions directly onto the surface of tooth enamel. While great advances were made in oral health care by the use of these various approaches, none seem to be completely effective.

A more recent approach to improved oral hygiene involves the recognition that bacteria present in the oral cavity metabolize dietary sugars, such as glucose and sucrose, to organic acids, such as acetic, propionic and lactic acids. The production of these acids results in a rapid drop in plaque pH. If the pH drops to a level of about 5.5 or below and remains there for more than a short period of time, the tooth enamel will begin to demineralize. This process, if repeated over a substantial period of time, will eventually lead to the development of caries. To correct for the pH drop, the saliva contains a pH-rise factor which moderates the extent and duration of the pH drop when glucose and sucrose are metabolized by oral bacteria. This factor was identified as an arginine-containing tetrapeptide. See, for example, Kleinberg, I., Kanapka, J. A., and Craw, D. "Effect of Saliva and Salivary Factors on the Metabolism of the Mixed Oral Flora" *Microbial Aspects of Dental Caries*, Vol. II, pp. 433-464 (1976). This pH-rise factor is believed to enter the bacterial cell and either neutralize the organic acids as they form or alter bacterial metabolism so that the acids are not produced.

DISCUSSION OF THE PRIOR ART

U.S. Pat. No. 2,689,170 to King, entitled "Oral Preparation for Inhibition of Dental Caries", discloses oral preparations for inhibition of dental caries having as the active ingredient a saturated higher series of alkyl acyl amide of a saturated aliphatic monoaminocarboxylic acid compound.

U.S. Pat. No. 4,154,813 to Kleinberg, entitled "Means and Method for Improving Natural Defenses Against Caries", discloses a method for supplementing the body's resistance to caries by providing a pH-rise factor which is a peptide of 2-4 amino acid units, one or more of which is arginine.

U.S. Pat. No. 4,225,579 to Kleinberg, entitled "Means and Method for Improving Defenses Against Caries", claims peptides of 2-4 amino acid units, one or more of which is arginine, for combatting caries. These arginine-containing peptides are disclosed to penetrate dental plaque and bacteria in the mouth and to counteract acid produced as a result of metabolism of carbohydrates.

British Pat. No. 1,352,420 to Yoshinaga et al, entitled "Novel Arginine Derivatives, their Production and their Use", discloses $N^\alpha$-acylarginines having antibacterial or germicidal properties for use in oral hygiene.

U.S. Pat. No. 3,809,759 to Bocher and Faure, entitled "Pharmaceutical Composition for Treating Mental Fatigue Containing Arginine-Potassium Phospho-Citro-Glutamate and Method of Using the Same", discloses arginine-potassium phospho-citro-glutamate in pharmaceutical compositions, such as, granules, pills, tablets, and capsules for systemic treatment of mental fatigue.

U.S. Pat. No. 4,061,542 to Demny and Maehr, entitled "2-Methyl-L-Arginine Produced by Cultivating Streptomyces Strain", discloses the title compound for use as an antibiotic and antibacterial agent.

U.S. Pat. No. 4,125,619 to Okamoto et al, entitled "$N^\alpha$-Naphthalenesulfonyl-L-Arginine Derivatives and the Pharmaceutically Acceptable Acid Addition Salts Thereof", discloses the title compounds for use as pharmaceutical agents for the inhibition and suppression of thrombosis.

Some long-chain $N^G$-acyl derivatives of arginine are described in the chemical literature. See for example, Guttmann, St. and Pless, J. "On the Protection of the Guanidino Group of Arginine", *Acta Chim Acad. Sci. Hung* 44 (1-2), 23-30 (1965). The acyl groups are temporarily placed on the arginine molecule at the $N^G$-position and serve as temporary blocking or protecting groups which are subsequently removed from the $N^G$-position when the appropriate substituents are placed on the $N^\alpha$-position of arginine. These blocking groups thus serve to protect the $N^G$-position from chemically reacting while the nitrogen atom at the $N^\alpha$-position participates in the chemical reaction.

The compounds of the present invention differ from the aforementioned prior art in that we use new and novel derivatives of arginine in which the polar character of the arginine molecule is modified by the presence of lipid-like substituents. This modification is believed to permit such arginine derivatives to more readily penetrate the phospholipid-containing cell wall of oral bacteria and to inhibit acid production of these bacteria.

Accordingly, one object of the present invention is to provide new and novel derivatives of arginine.

Another object of the present invention is to provide compositions containing an arginine derivative for use in oral applications.

Still another object of the present invention is to provide compositions containing an arginine derivative in combination with a fluoride compound for use in oral applications.

It is still a further object of the present invention to provide methods of preparing such compounds and compositions.

SUMMARY OF THE INVENTION

Oral compositions of the present invention comprise $N^G$-acyl derivatives of arginine of the formula:

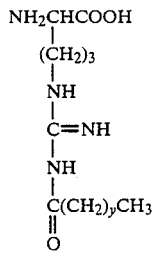

where y is an integer from 0 to about 28, preferably from about 4 to about 18, and most preferably from 8 to 14.

The $N^G$-acyl derivatives of arginine where y is not more than about 18 are preferred since these derivatives possess greater activity against oral bacteria than the higher members of the series.

In general, $N^G$-acyl derivatives of arginine may be prepared by first preparing the sodium salt of $N^\alpha$-CbZ-L-arginine. This salt is then allowed to react in a mole ratio of 2:1 with an aliphatic acid chloride or in a mole ratio of 1:1 with an ethyl ester or a succinimidyl ester of an aliphatic acid. The crude $N^\alpha$-CbZ-$N^G$-acyl derivative is isolated by pouring the reaction mixture into ice water and acidifying with glacial acetic acid. The crude derivative is then purified by recrystallization from methanol and the $N^\alpha$-CbZ group is removed by catalytic hydrogenolysis.

The present invention also encompasses pharmaceutically acceptable salts of the $N^G$-acyl derivatives of arginine such as those formed by reaction of an organic or inorganic base with the acidic (—COOH) portion of the acylarginine molecule, and those formed by reaction of an organic or inorganic acid with the basic amino or guanidino portions of the acylarginine molecule. Typical salts are those of the formula

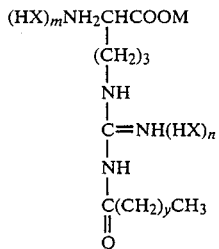

wherein y is an integer of from 0 to about 28; M is H, Na, K, Mg, Ca, Ag, Ce, Mn, Zn or the residue of a strong organic base; m and n are 0 or 1; and HX is HCl, $HNO_3$, $H_2SO_4$, $CH_3COOH$ or gluconic acid

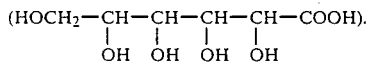

The present invention provides oral compositions of an $N^G$-acyl derivative of arginine in the form of a mouthwash, spray, dentifrice, gel, powder, solution, lotion, varnish, lozenge, chewing gum, slow releasing device and the like for use in oral hygiene.

The present invention further provides oral compositions of $N^G$-acyl derivatives of arginine with a fluoride compound, such as, sodium fluoride, zinc fluoride, stannous fluoride, sodium monofluorophosphate, acidulated phosphate fluoride, ammonium fluoride, ammonium bifluoride and amine fluoride.

DETAILED DESCRIPTION OF THE INVENTION $N^G$-acyl derivatives of arginine are prepared according to the following general procedure.

The sodium salt of $N^\alpha$-CbZ-L-arginine is prepared by reacting $N^\alpha$-CbZ-L-arginine with sodium ethoxide in ethanol and evaporating to dryness. The dry salt is dissolved in N,N-dimethylformamide and the solution cooled to 5° C. An aliphatic acid chloride in DMF is added dropwise to the cold solution to provide a mole ratio of acid chloride to $N^\alpha$-CbZ-L-arginine sodium salt of 1:2. The reaction mixture is brought to room temperature and stirred for 24 hours. The mixture is then chilled and diluted by pouring into ice water, and a solid product precipitated by adjusting the pH to 5 using glacial acetic acid. The precipitated solid is washed with water and allowed to air dry, then recrystallized from an organic solvent such as ethanol. The recrystallized solid which is pure $N^\alpha$-CbZ-$N^G$-acylarginine is dissolved in a mixture of ethanol and glacial acetic acid. After adding a palladium-on-carbon catalyst, the mixture is shaken in an atmosphere of hydrogen gas and the $N^\alpha$-CbZ group removed by catalytic hydrogenolysis. The solution is then filtered and the filtrate evaporated to dryness. The residual solid is recrystallized from 95% ethanol to obtain the desired $N^G$-acyl derivative of arginine.

A more complete understanding of the process for preparing compounds of this invention and oral compositions comprising such compounds will be obtained by reference to the following specific examples, which are included for purposes of illustration only and are not intended to be limiting.

EXAMPLE 1

Preparation of $N^G$-decanoylarginine 50.00 g (0.1622 mole) of $N^\alpha$-CbZ-L-arginine were suspended in 100 ml of absolute ethanol. To this suspension was added, in one portion, a solution of sodium ethoxide prepared by reacting 3.73 g (0.162 mole) of sodium metal with 100 ml of absolute ethanol. The mixture was vigorously stirred at room temperature until all the solid had dissolved. The solution was then evaporated to dryness, first using a rotary evaporator at 40°, followed by more complete drying under vacuum at room temperature to obtain the sodium salt of $N^\alpha$-CbZ-L-arginine as a white solid. This material was dissolved in 200 ml of dry N,N-dimethylformamide and placed in a 1-liter, 3-neck flask equipped with mechanical stirrer, drying tube and addition funnel. A solution of 15.47 g (0.0811 mole) of decanoyl chloride in 25 ml of dry DMF was then added dropwise during 1.5 hr. while the reaction mixture was kept at 5° using an ice bath. When addition was complete, the mixture was allowed to slowly warm to room temperature and was stirred at room temperature for 24 hrs. The mixture was filtered to remove insoluble material, poured over 1,000 g of a mixture of ice and water, and the bright yellow solution acidified with glacial acetic acid (the pH was changed from 9 to 5 during this process). A solid precipitated at this stage; it quickly became gummy and adhered to the walls and bottom of the beaker. The water and ice were poured off and the wet solid was treated with approximately 1,000 ml of absolute methanol. This mixture was heated on a hot plate until all the solid dissolved, and then slowly cooled to room temperature. The solid which crystallized during the cooling process was collected by filtration and identified as pure $N^\alpha$-CbZ-$N^G$-decanoylarginine having the formula:

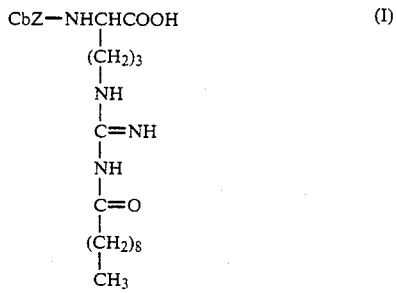

Compound (I) (2.77 g, 5.99 mmol) was dissolved in a solution of 30 ml glacial acetic acid and 100 ml of abs. ethanol. To this solution was added a suspension of 0.25 g 10% palladium on activated carbon in 10 ml glacial acetic acid. This mixture was treated with hydrogen gas by vigorously stirring the suspension while blowing hydrogen gas continuously over the surface. The catalytic hydrogenolysis was monitored for cessation of carbon dioxide evolution by bubbling the effluent gasses through a saturated barium hydroxide solution. When the reaction was complete, the mixture was filtered through Celite to remove the catalyst. The filtrate was evaporated to dryness, first on a rotary evaporator at 40°, and finally under vacuum at room temperature. The dry residue was recrystallized from 95% ethanol to yield 1.94 g (83.3%) of $N^G$-decanoylarginine as the acetic acid salt having the formula:

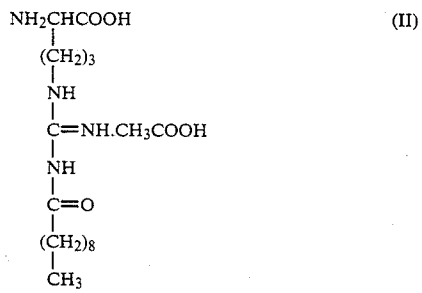

Exactly the same procedure was used to prepare the following $N^G$-acyl derivatives of arginine:
$N^G$-octanoylarginine ($C_8$)
$N^G$-nonanoylarginine ($C_9$)
$N^G$-undecanoylarginine ($C_{11}$)
$N^G$-lauroylarginine ($C_{12}$)
$N^G$-myristoylarginine ($C_{14}$)
$N^G$-palmitoylarginine ($C_{16}$)
$N^G$-stearoylarginine ($C_{18}$)
$N^G$-eicosanoylarginine ($C_{20}$).
It is also possible to prepare $N^G$-acyl derivatives of arginine by reacting the sodium salt of $N^\alpha$-CbZ-L-arginine with the ethyl ester or the succinimidyl ester of the desired aliphatic acid instead of the acid chloride. This is illustrated in Examples 2 and 3.

EXAMPLE 2

The sodium salt of $N^\alpha$-CbZ-L-arginine was prepared from 12.03 g (0.0390 mole) of $N^\alpha$-CbZ-L-arginine as described in Example 1, and dissolved in 50 ml of dry DMF. To this solution was added, dropwise, during 15 minutes, 10.00 g (0.039 mole) of ethyl myristate, followed by rapid addition of 10 ml of DMF. The reaction mixture was stirred at room temperature for 48 hours, then poured over 1,000 g of a mixture of ice and water. This basic mixture (pH 12) was acidified with glacial acetic acid to a pH of 5. A pale yellow, slightly gummy solid immediately precipitated. This was collected by gravity filtration and was dried in an oven at 45°. The dry solid was recrystallized from absolute methanol to obtain pure $N^\alpha$-CbZ-$N^G$-myristoylarginine which was dissolved in a 50:50 mixture of glacial acetic acid/ethanol and subjected to catalytic hydrogenolysis as described in Example 1.

EXAMPLE 3

The sodium salt of $N^\alpha$-CbZ-L-arginine was prepared from 12.03 g (0.0390 mole) of $N^\alpha$-CBZ-L-arginine as described in Example 1 and dissolved in 50 ml of dry DMF. To this solution was added, dropwise, during 15 minutes, 12.69 g (0.039 mole) of succinimidyl myristate, followed by rapid addition of 10 ml of DMF. The reaction mixture was stirred at room temperature for 24 hours, then poured over 1,000 g of a mixture of ice and water. This basic mixture (pH 12) was acidified with glacial acetic acid to a pH of 5. A pale yellow, slightly gummy solid immediately precipitated. This was collected by gravity filtration and was dried in an oven at 45°. The dry solid was recrystallized from absolute methanol to obtain pure $N^\alpha$-CbZ-$N^G$-myristoylarginine which was dissolved in a 50:50 mixture of glacial acetic acid/ethanol and subjected to catalytic hydrogenolysis as described in Example 1.

Representative compounds of the present invention were assayed to determine their effectiveness in reducing acid production from sugar by *S. mutans* as a measure of their efficacy in oral compositions.

ASSAY FOR INHIBITORS OF GLYCOLYSIS

This assay measures the rate of acid production from the metabolism of sucrose by Streptococcus mutans 6715. The assay solution consists of 10.00 ml of a phosphate buffer at pH 5.5 under nitrogen. To this solution are added $8 \times 10^9$ cells of *S. mutans* 6715, followed by 50 μl of $25 \times 10^{-3}$M sucrose. A known volume of a 10 mg/ml solution of the test arginine derivative is then added, and the rate of acid production is monitored with the automatic addition of a $5 \times 10^{-3}$N KOH solution by a pH-stat.

Table I illustrates acid inhibition activity of the compounds indicated.

TABLE I

| Arginine Derivative | Concentration (W/V %) | Reduction in Rate of Acid Formation (%) |
|---|---|---|
| $N^G$—Octanoylarginine | 3.0 | 55 |
| $N^G$—Nonanoylarginine | 2.0 | 43 |
| $N^G$—Decanoylarginine | 6.0 | 67 |
| $N^G$—Undecanoylarginine | 2.0 | 80 |
| $N^G$—Lauroylarginine | 1.0 | 100 |
| $N^G$—Myristoylarginine | 0.5 | 100 |

TABLE I-continued

| Arginine Derivative | Concentration (W/V %) | Reduction in Rate of Acid Formation (%) |
|---|---|---|
| $N^G$—Palmitoylarginine | 3.0 | 29 |
| $N^G$—Stearoylarginine | 1.0 | 33 |

The combination of $N^G$-acyl derivatives of arginine with a fluoride compound, e.g. sodium fluoride, zinc fluoride, stannous fluoride, sodium monofluorophosphate, acidulated phosphate fluoride, ammonium fluoride, ammonium bifluoride and amine fluoride is more effective in preventing the development of caries in rodents than either compound alone. While both NaF and $N^G$-acyl derivative of arginine were effective in preventing the development of caries in the rodent model when they were used alone under the given test conditions, the combination of the above two ingredients resulted in a substantially enhanced anticaries activity. The results of this test are summarized in Table II.

TABLE II

Anticaries Activity of $N^G$—Myristoylarginine

| Test Composition | Total Caries Lesions | % Reduction in Total Lesions | Severity of Caries Lesions | % Reduction in Severity of Lesions |
|---|---|---|---|---|
| Control[(1)] | 11.1 ± 0.81 | 0 | 31.9 ± 2.68 | 0 |
| Example 5 | 10.1 ± 0.94 | 8 | 29.1 ± 2.97 | 9 |
| Control + 0.22% NaF | 8.1 ± 0.80 | 26 | 24.1 ± 2.50 | 24 |
| Example 6 | 6.5 ± 0.81 | 41 | 18.9 ± 2.52 | 41 |

[(1)]The composition of the control is the same as in Example 5 without the $N^G$—acylarginine.

In general, the $N^G$-acyl derivative of arginine should be present in an effective amount up to a saturated solution, while the fluoride ion should be present from as low as 0.0001% to 10%.

The preferred concentration of the $N^G$-acyl derivative of arginine is 0.05 to 10%, while that of the fluoride ion is 0.001 to 1.0%. The most preferred concentration of $N^G$-acyl derivative of arginine is 0.5 to 5%, and the fluoride ion, 0.01 to 0.1%. While higher concentrations of both $N^G$-acyl derivatives of arginine and fluoride ions could be used, no particular advantage is afforded thereby.

While it is presently preferred to have a polyol-containing aqueous vehicle as an acceptable carrier for the above composition, other nonaqueous compositions are not excluded from the list of suitable carriers, as for example various alcohols, polyols, and dimethylsulfoxide.

The composition of this invention may be in the form of a mouthwash, spray, dentifrice, gel, powder, solution, lotion, varnish, lozenge, chewing gum, slow releasing device or other forms suitable for oral application. Any pharmaceutically acceptable materials such as those ordinarily used in such oral compositions that are compatible with $N^G$-acyl derivatives of arginine and fluoride ions may be employed in the compositions of this invention.

In accordance with the present invention, the compositions are supplied to teeth with an appliance, e.g., toothbrush, swab, impregnated dental floss and the like by gently brushing the teeth, both the buccal and lingual sides, at least once daily. The most preferred application of the above compositions to teeth is from lozenge and from chewing gum, whereby one slowly dissolves the lozenge in the mouth over 10 to 15 minutes, and by chewing the gum over 30 to 45 minutes after each meal.

The following examples will further serve to illustrate typical oral compositions of this invention.

EXAMPLE 4 (Mouthrinse)

| | w/w % |
|---|---|
| Glycerol, U.S.P. | 10 to 40 |
| $N^G$—acylarginine | 0.1 to 5 |
| NaF | 0.2 |
| Flavors | 1.0 |
| Preservatives | 0.3 |
| Pluronic F-108 | 2.0 |
| Water, q.s. to 100 parts | |

The $N^G$-acyl derivative of arginine was dissolved in water with continuous stirring at 80° C. The remaining ingredients were dissolved in glycerol and mixed with the $N^G$-acylarginine solution at room temperature.

EXAMPLE 5 (Gel Dentifrice)

| | w/w % |
|---|---|
| Pluronic F-127 | 20.0 |
| Flavors | 0.8 |
| Preservatives | 0.3 |
| $N^G$—acylarginine | 2.0 |
| Water, q.s. to 100 parts | |

EXAMPLE 6 (Gel Dentifrice)

| | w/w % |
|---|---|
| $N^G$—acylarginine | 2.0 |
| NaF | 0.2 |
| Pluronic F-127 | 20.0 |
| Flavors | 0.8 |
| Preservatives | 0.3 |
| Water, q.s. to 100 parts | |

The gels of Examples 5 and 6 were prepared as follows:

The $N^G$-acylarginine was dissolved in 50 ml water while continuously stirring at 80° C. After the arginine derivative had dissolved, the solution was cooled to room temperature and the NaF (if present) and preservatives were added. Separately, the Pluronic F-127 and flavors were dissolved at 4° C. The solution was allowed to warm up to room temperature and then blended into the arginine containing solution with continuous stirring. The mixture was homogenized and the pH of the gel adjusted to 5.5 by the addition of NaOH or HCl as required.

EXAMPLE 7 (Paste Dentifrice)

| | w/w % |
|---|---|
| $N^G$—acylarginine | 1 to 5 |
| NaF | 0.2 |
| Glycerol | 15.0 |
| Sorbitol | 10.0 |
| Sodium lauryl sulfate | 1.2 |
| Calcium pyrophosphate | 40.0 |
| Propylene glycol | 10.0 |
| Flavors | 1.0 |
| Preservatives | 0.3 |
| Pluronic F-127 | 10.0 |

| | w/w % |
|---|---|
| Water, q.s. to 100 parts | |

The $N^G$-acylarginine was dissolved in glycerol, sorbitol, propylene glycol, Pluronic F-127 and water at 80° C. The pH was adjusted to 5.5 and the flavors, NaF, preservatives and sodium lauryl sulfate were added. The calcium pyrophosphate was blended into the mixture with continuous stirring at room temperature, and the mixture was homogenized with a roller mill. In this formulation, the sodium fluoride component is optional and may be omitted in the preparation of a non-fluoride dentifrice.

EXAMPLE 8 (Powder Dentifrice)

| | w/w % |
|---|---|
| $N^G$—acylarginine | 1 to 5 |
| Flavors | 4.0 |
| Sodium lauryl sulfate | 2.0 |
| Saccharin | 0.4 |
| Abrasive, q.s. to 100 parts | |

EXAMPLE 9 (Lozenge)

| | w/w % |
|---|---|
| $N^G$—acylarginine | 1 to 5 |
| Sorbitol | 20.0 |
| Mannitol | 20.0 |
| Starch | 12.0 |
| Flavors | 2.0 |
| Preservatives | 0.4 |
| Saccharin | 0.2 |
| Magnesium stearate | 0.8 |
| Talc | 0.5 |
| Corn syrup, q.s. to 100 parts | |

The mixture of Example 9 was granulated into a homogeneous blend and pressed into a lozenge.

Although the present invention has been described with reference to particular embodiments and examples, it will be apparent to those skilled in the art that variations and modifications of this invention can be made and that equivalents can be substituted therefore without departing from the principles and the true spirit of the invention.

We claim:

1. $N^G$-acyl derivatives of arginine having the formula:

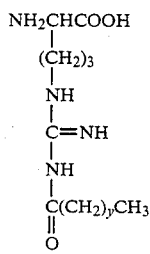

where y is an integer of from 0 to 28, and the pharmaceutically acceptable salts thereof.

2. A compound of claim 1 wherein said pharmaceutically acceptable salts are selected from the group consisting of alkali metal salts, alkaline earth metal salts, amphoteric metal salts, heavy metal salts, organic base salts, and organic and inorganic acid salts.

3. The compound of claim 1 wherein said $N^G$-acyl derivative of arginine is $N^G$-octanoylarginine.

4. The compound of claim 1 wherein said $N^G$-acyl derivative of arginine is $N^G$-nonanoylarginine.

5. The compound of claim 1 wherein said $N^G$-acyl derivative of arginine is $N^G$-decanoylarginine.

6. The compound of claim 1 wherein said $N^G$-acyl derivative of arginine is $N^G$-undecanoylarginine.

7. The compound of claim 1 wherein said $N^G$-acyl derivative of arginine is $N^G$-lauroylarginine.

8. The compound of claim 1 wherein said $N^G$-acyl derivative of arginine is $N^G$-myristoylarginine.

9. The compound of claim 1 wherein said $N^G$-acyl derivative of arginine is $N^G$-palmitoylarginine.

10. The compound of claim 1 wherein said $N^G$-acyl derivative of arginine is $N^G$-stearoylarginine.

11. The compound of claim 1 wherein said $N^G$-acyl derivative of arginine is $N^G$-eicosanoylarginine.

12. A composition of matter for oral hygiene to inhibit acid production by microorganisms in the oral cavity comprising an effective amount, in a pharmaceutically acceptable carrier, of an $N^G$-acyl derivative of arginine having the formula;

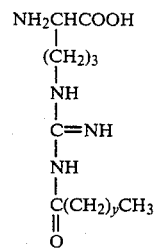

wherein y is an integer of from 0 to 28, or a pharmaceutically acceptable salt thereof.

13. The composition of matter of claim 12 wherein said $N^G$-acyl derivative of arginine is $N^G$-octanoylarginine.

14. The composition of matter of claim 12 wherein said $N^G$-acyl derivative of arginine is $N^G$-nonanoylarginine.

15. The composition of matter of claim 12 wherein said $N^G$-acyl derivative of arginine is $N^G$-decanoylarginine.

16. The composition of matter of claim 12 wherein said $N^G$-acyl derivative of arginine is $N^G$-undecanoylarginine.

17. The composition of matter of claim 12 wherein said $N^G$-acyl derivative of arginine is $N^G$-lauroylarginine.

18. The composition of matter of claim 12 wherein said $N^G$-acyl derivative of arginine is $N^G$-myristoylarginine.

19. The composition of matter of claim 12 wherein said $N^G$-acyl derivative of arginine is $N^G$-palmitoylarginine.

20. The composition of matter of claim 12 wherein said $N^G$-acyl derivative of arginine is $N^G$-stearoylarginine.

21. The composition of matter of claim 12 wherein said $N^G$-acyl derivative of arginine is $N^G$-eicosanoylarginine.

22. The composition of matter of claim 12 wherein said pharmaceutically acceptable carrier is a dentifrice.

23. The composition of matter of claim 12 wherein said pharmaceutically acceptable carrier is a lozenge.

24. A composition of matter for oral hygiene to inhibit the formation of caries comprising, in a pharmaceutically acceptable carrier, from about 0.0001% to about 10% of a fluoride salt and an effective amount of a $N^G$-acyl derivative of arginine having the formula:

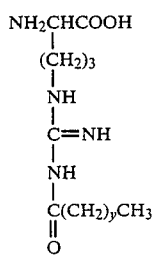

wherein y is an integer of from 0 to 28, or a pharmaceutically acceptable salt thereof.

25. The composition of matter of claim 24 wherein said pharmaceutically acceptable carrier is a mouthrinse.

26. The composition of matter of claim 24 wherein said pharmaceutically acceptable carrier is a dentifrice.

27. A composition of matter for oral hygiene to inhibit the formation of caries comprising from about 0.05 to about 10% of $N^G$-acyl derivative of arginine having the formula:

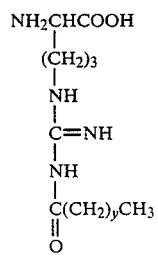

wherein y is an integer of from 4 to 18, or a pharmaceutically acceptable salt thereof, in combination with from about 0.001 to about 1.0% of a fluoride salt in a pharmaceutically acceptable polyol-containing vehicle.

28. The composition of matter of claim 27 wherein said $N^G$-acyl derivative of arginine is $N^G$-lauroylarginine.

29. The composition of matter of claim 27 wherein said $N^G$-acyl derivative of arginine is $N^G$-myristoylarginine.

30. A method for inhibiting acid production by microorganisms in the oral cavity which comprises introducing into the oral cavity in a pharmaceutically acceptable carrier, an effective amount of an $N^G$-acyl derivative of arginine having the formula:

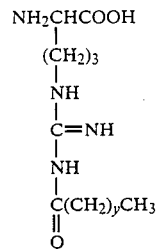

wherein y is an integer of from 0 to 28, or a pharmaceutically acceptable salt thereof.

31. A method for inhibiting acid production by microorganisms in the oral cavity which comprises introducing into the oral cavity a composition comprising, in a pharmaceutically acceptable carrier, from about 0.0001% to about 10% of a fluoride salt and an effective amount of an $N^G$-acyl derivative of arginine having the formula:

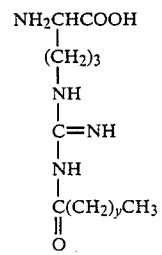

wherein y is an integer of from 6 to 29, or a pharmaceutically acceptable salt thereof.

32. A method for inhibiting acid production by microorganisms in the oral cavity which comprises introducing into the oral cavity a composition comprising from about 0.05 to about 10% of $N^G$-acyl derivative of arginine having the formula:

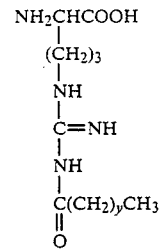

wherein y is an integer of from 4 to 18, or a pharmaceutically acceptable salt thereof, in combination with from about 0.001 to about 1.0% of a fluoride salt in a pharmaceutically acceptable polyol-containing vehicle.

* * * * *